United States Patent [19]

Wald et al.

[11] 4,166,189

[45] Aug. 28, 1979

[54] PRODUCTION OF METHYL ESTERS BY CONTACTING METHANOL OR DIMETHYL ETHER WITH CARBON MONOXIDE AND ZINC IODIDE

[75] Inventors: Milton M. Wald; Leo Kim, both of Houston, Tex.

[73] Assignee: Shell Oil Company, Houston, Tex.

[21] Appl. No.: 899,056

[22] Filed: Apr. 24, 1978

[51] Int. Cl.$^2$ .................. C07C 67/36; C07C 67/37
[52] U.S. Cl. .......................... 560/232; 260/652 R; 560/233; 585/409; 585/733; 585/943
[58] Field of Search ............. 560/232, 233; 260/532, 260/533 A; 562/517, 519, 521

[56] References Cited

U.S. PATENT DOCUMENTS 1,562,480  11/1925  Wietzel et al. .................. 560/232

FOREIGN PATENT DOCUMENTS 1167116  10/1969  United Kingdom .............. 260/533 A Primary Examiner—Vivian Garner
Attorney, Agent, or Firm—Howard W. Haworth; Ronald L. Clendenen

[57] ABSTRACT

Method for the production of branched chain esters comprising contacting methanol and/or dimethyl ether and carbon monoxide with zinc iodide at a temperature of from about 180° C. to 450° C. Improved selectivity to methyl pivalate is obtained by incorporating ethylene, propylene and/or isobutylene into the reaction mixture.

6 Claims, No Drawings

PRODUCTION OF METHYL ESTERS BY CONTACTING METHANOL OR DIMETHYL ETHER WITH CARBON MONOXIDE AND ZINC IODIDE

BACKGROUND OF THE INVENTION

1. Field of the Invention

This invention relates to a method of producing branched chain esters as for example methyl-2,2,3,3-tetramethylbutyrate, from methanol and carbon monoxide.

2. Description of the Prior Art

Previous efforts to convert methanol to higher carbon number molecules have led to hydrocarbons rather than esters. Even this prior experimental work with methanol conversion to hydrocarbons may be characterized as largely academic or substantially uneconomic in present terms. For example, as early as 1878, LeBel and Green (Compt. Rend. Vol. 87, p. 260) produced alkyl hydrocarbons by contacting methanol with zinc chloride at elevated temperatures. More recently, Grosse and Snyder describe and claim a process in U.S. Pat. No. 2,492,984 wherein a mixture consisting essentially of a specified metal halide and at least one compound selected from the group consisting of methanol and dimethyl ether is subjected to conversion conditions, including a temperature of 250° C. to 650° C., to form substantial amounts of recoverable hydrocarbons having at least four carbon atoms. The examples of the patent employ a zinc chloride catalyst, and the specification mentions that higher atomic weight halides of metals such as zinc, cadmium, thorium, and the like, may be used.

Normally, methanol conversion in zinc halides results in alkanes and alkenes, even when conducted in the presence of olefins, e.g. see U.S. applications Ser. No. 850,872 and 850,874 both filed on Nov. 14, 1977, as well as U.S. Pat. No. 4,059,647 issued Nov. 22, 1977. The particular advantage of this invention is that carboxylic acid esters are also produced. The highly branched ester products of the invention find use as solvents and chemical intermediates.

SUMMARY OF THE INVENTION

Accordingly, the invention provides a method for the production of branched chain esters by reacting methanol, dimethyl ether or mixtures thereof with carbon monoxide at a ratio of carbon monoxide to methanol of greater than 0.25 in the presence of zinc iodide, at a temperature of from about 180° C. to about 450° C. The use of zinc bromide does not give the same beneficial results. The invention produces methyl esters of branched acids having carbon numbers from about five to about eight. The invention particularly produces methyl pivalate ((CH$_3$)$_3$CCOOCH$_3$) and methyl-2,2,3,3-tetramethylbutyrate ((CH$_3$)$_3$CC(CH$_3$)$_2$COOCH$_3$) in major amounts. Addition of ethylene, propylene, isobutylene and mixtures thereof to the reaction mixture results in an increase in methyl pivalate production.

DESCRIPTION OF THE PREFERRED EMBODIMENT

The source of the methanol employed is a matter of choice. For example, methanol derived from synthesis gas produced from coal, and methanol produced from natural gas are eminently suited to the practice of the invention. The purity of the methanol is not critical, provided the impurities do not interfere with the reaction. Thus, small amounts of water and ethanol, common impurities in methanol, do not interfere. In general, dilute streams of methanol may be used, provided, as noted, the diluents do not interfere with the activity of the zinc iodide. The term "methanol", as used in the specification and claims, is intended to include the use of such dilute streams containing methyl alcohol. Moreover, any material which will react to provide methanol in situ under the reaction conditions specified herein, and which does not interfere with the reaction, and whose other reaction product or products, if any, do not interfere with the reaction, is within the scope of the invention. For example, dimethyl ether may be used as a source of methanol, either as the total feed, or a portion thereof. Under some conditions, disclosed herein, significant quantities of dimethyl ether may be formed. This dimethyl ether may be separated and recycled, thereby providing a highly efficient use of source materials.

The carbon monoxide utilized in this invention may be pure or mixed with gases that are inert to the reaction conditions. Synthesis gas can provide an excellent source of carbon monoxide. Significant amounts of hydrogen do not interfere with the reaction. The carbon monoxide partial pressure in the reaction mixture is maintained at partial pressure greater than 100 psia, preferably greater than 1000 psia. The molar ratio of carbon monoxide to methanol or dimethyl ether must be kept relatively high to favor the formation of branched chain esters. The ratio of carbon monoxide to methanol should be greater than 0.25 and preferably greater than 10.

Lower carbon number olefins may be introduced into the reaction mixture to provide an increase in methyl pivalate production. Preferred olefins are ethylene, propylene and isobutylene, with isobutylene being particularly preferred.

The zinc iodide need not be pure, but may contain impurities which do not interfere with the reaction. Commercial grade zinc iodide is acceptable in the process of the invention.

Temperatures employed in the reaction range from about 180° C. to about 450° C., preferably from about 190° C. to about 350° C. and most preferably from about 200° C. to about 280° C.

The ratio of olefin when utilized to methanol is widely variable, and those skilled in the art may vary the proportions as desired. Thus, a ratio of 0.1 mols to 25 mols of methanol per mol of olefin may be employed, with a ratio of from 0.3 mols to 10 mols of methanol per mol of olefin being preferred. At the same time, however, the appropriate ratio of methanol to ZnI$_2$, i.e., in an amount sufficient to initiate and sustain the reaction, must be employed. Those skilled in the art may readily determine appropriate amounts, keeping in mind that excessively high ratios of reactants, especially methanol to ZnI$_2$, or mixtures thereof, may not be used. For example, ratios of from about 0.01 mol of methanol per mol of ZnI$_2$ to about 24 mols of methanol per mol of ZnI$_2$ may be used, while ratios of from about 0.1 mol of methanol per mol of ZnI$_2$ to about 10 mols of methanol per mol of ZnI$_2$ are preferred. Where dimethyl ether is used as a feed, the ratio of feed to ZnI$_2$ would be similar, and where dimethyl ether is used as a portion of the feed, adjustment of the feed ratio may be made readily.

The process may be conducted batch-wise or in a continuous fashion. Whichever procedure is employed, good mixing or contact of the $ZnI_2$ and the reactants is important for good results. Any reaction system which provides a high degree of mixing or contact of reactants may be employed. For example, fixed bed systems, slurry reactors, and trickle bed reactors may be used. Contact times are not critical, and those skilled in the art may vary the contact times to provide sufficient contact time to produce optimum results, depending on, e.g., volume of reactants, reactor design, temperature, etc. For example, utilizing a fixed bed reactor design, and continuous flow of reactants, contact times on the order of from about 0.5 minute (245° C.) to about 120 minutes, or 180 minutes (200° C.), or even longer, may be used. Where batch procedures are employed, contact times may be considerably longer. In both batch and continuous procedures, it is not necessary that 100 percent conversion of the methanol be obtained before recovering the product, the methanol being easily separable and recyclable.

The process of this invention is described by the following illustrative embodiments which are provided for illustration and are not to be construed as limiting the invention.

EXAMPLE 1

A clean, dry 300 ml Hastelloy B Magna-Drive autoclave was loaded with 200 g $ZnI_2$. It was sealed and pressure tested with $N_2$. It was then pressured to 980 psig with carbon monoxide at 25° C. It was heated to 190° C. and stirred at 1500 rpm. Pressure was about 1700 psig. Methanol was pumped in at about 2 ml/min via a Hastelloy C dip tube extending nearly to the bottom of the autoclave. 56 Milliliters (44 grams) were pumped in over a 25 minute period. There was a brief exotherm during the early part of the methanol addition, with the temperature rising to 225° C. It was lined out at 200° C. soon thereafter. Pressure during the methanol addition rose to 2140 psig (at 200° C.). After the methanol was added, the reactor was maintained at 200° C. and stirred for 35 minutes more (total reaction time 60 minutes). Pressure at the end of the heating period was 1975 psig. The reactor was cooled back to 25° C. and pressure dropped to 1090 psig. The gas present was vented and collected for volume measurement and analyses. The liquid product was distilled into a cold trap by heating (and stirring) the autoclave at 140°-150° C. under slow $N_2$ bleed. When no more liquid appeared to be coming over, the temperature was raised to 200° C. for 15 minutes and then to 250° C. for 15 minutes more. The liquid in the cold trap weighed 44.15 g and had two layers. The isolated upper (organic) layer weighed 16.49 g and lower (aqueous) layer weighed 26.19 g.

Analysis (GLC and mass spectrographic) of the gaseous and liquid products indicated the following product yields, stated as grams of products per 100 grams of methanol feed:

$CH_4$: 0.2
i-$C_4H_{10}$: 5.3
i-$C_5H_{12}$: 1.2
$C_6H_{14}$: 1.4
2,2,3-trimethylbutane: 18.7
Other $C_7$ & $C_8$ hydrocarbons: 2.0
$C_9$-$C_{13}$ hydrocarbons: 8.4
Hexamethylbenzene: 4.7
$CH_3I$: 25.0
$CO_2$: 2.9
Methyl pivalate: 7.7
Methyl ester of $C_5H_{11}COOH$: 3.9
Methyl ester of $C_6H_{13}COOH$: 2.8
Methyl 2,2,3,3-tetramethylbutyrate: 24.0

EXAMPLE 2

Example 1 was repeated using 200 g of $ZnBr_2$ instead of the $ZnI_2$. The temperature of the reactor was lined out at 235° C. to compensate for known lower activity of $ZnBr_2$. No significant amount of esters was found.

EXAMPLE 3

Example 1 was repeated using a reactant feed of 20.0 g of methanol plus 37 g of isobutylene, pumped at 2 ml/min. Product analysis showed the same four esters present as in example 1 but with the methyl pivalate being present in the largest amount.

We claim as our invention:

1. A method for the production of methyl esters of branched acids having a carbon number from about five to about eight comprising contacting a material selected from the group consisting of methanol; dimethyl ether and mixtures thereof, with carbon monoxide and zinc iodide at a temperature of from about 180° C. to about 450° C. wherein the molar ratio of carbon monoxide to methanol or dimethyl ether is greater than 0.25.

2. The method of claim 1 wherein the temperature is from about 190° C. to about 350° C.

3. The method of claim 2 wherein the temperature is from about 200° C. to about 280° C.

4. The method of claim 1 wherein the molar ratio of carbon monoxide to methanol, or dimethyl ether is greater than 10.

5. The method of claim 1 wherein ethylene, propylene, isobutylene or mixtures thereof are additionally contacted therein.

6. The method of claim 5 wherein isobutylene is additionally contacted therein.

* * * * *